United States Patent [19]
Riechers et al.

[11] Patent Number: 6,064,903
[45] Date of Patent: May 16, 2000

[54] ELECTROMAGNETIC DETECTION OF AN EMBEDDED DIELECTRIC REGION WITHIN AN AMBIENT DIELECTRIC REGION

[75] Inventors: Ronald George Riechers, Beavercreek; Krishna Murthy Pasala, Dayton, both of Ohio

[73] Assignee: Spectra Research, Inc., Dayton, Ohio

[21] Appl. No.: 09/221,337

[22] Filed: Dec. 28, 1998

Related U.S. Application Data

[60] Provisional application No. 60/068,983, Dec. 29, 1997.

[51] Int. Cl.[7] ....................................................... A61B 5/00
[52] U.S. Cl. .......................... 600/407; 600/430; 324/638; 324/642
[58] Field of Search ................................... 600/407, 430; 324/637, 638, 629, 633, 642

[56] References Cited

U.S. PATENT DOCUMENTS

| | | | |
|---|---|---|---|
| 3,549,986 | 12/1970 | Prine | 324/629 |
| 3,836,846 | 9/1974 | Overall et al. | |
| 3,936,736 | 2/1976 | Ray | |
| 4,200,921 | 4/1980 | Buckley | 367/87 |
| 4,344,440 | 8/1982 | Aaby et al. | |
| 4,345,202 | 8/1982 | Nagy et al. | |
| 4,346,716 | 8/1982 | Carr | |
| 4,384,480 | 5/1983 | Krage et al. | 73/116 |
| 4,428,229 | 1/1984 | Storwick | 73/119 A |
| 4,468,956 | 9/1984 | Merlo | 73/117.3 |
| 4,557,272 | 12/1985 | Carr | |
| 5,078,714 | 1/1992 | Katims | 606/38 |
| 5,281,814 | 1/1994 | Weiss et al. | 250/306 |
| 5,417,494 | 5/1995 | Kempa et al. | 374/5 |
| 5,434,842 | 7/1995 | Weiss et al. | 369/126 |
| 5,448,243 | 9/1995 | Bethke et al. | 342/59 |
| 5,482,041 | 1/1996 | Wilk et al. | |
| 5,502,393 | 3/1996 | Yamaguchi et al. | 324/639 |
| 5,504,366 | 4/1996 | Weiss et al. | 73/863 |
| 5,539,322 | 7/1996 | Zoughi | 324/644 |
| 5,581,191 | 12/1996 | Yamaguchi | 324/637 |
| 5,619,035 | 4/1997 | Weiss et al. | 250/306 |
| 5,829,437 | 11/1998 | Bridges | |

*Primary Examiner*—Ruth S. Smith
*Attorney, Agent, or Firm*—Killworth, Gottman, Hagan & Schaeff, LLP

[57] ABSTRACT

A system for and method of electromagnetically detecting an embedded dielectric region within a target object are provided. The method includes the steps of: (i) selecting a target object including a plurality of discrete scattering mediums, wherein the plurality of discrete scattering mediums include the embedded dielectric region and an adjacent dielectric region, and wherein the plurality of discrete scattering mediums define at least one dielectric interface between the embedded dielectric region and the adjacent dielectric region; (ii) directing electromagnetic radiation at the target object, wherein the electromagnetic radiation is characterized by a diagnostic frequency that is varied incrementally over a diagnostic frequency band; (iii) detecting electromagnetic radiation reflected by the target object over the predetermined frequency band such that there are M measurements of a reflected electromagnetic signal at frequencies $f_1$, $f_2$, ..., $f_N$, where M represents a number of scattering mediums within the target object and where N represents a number of diagnostic frequencies within the diagnostic frequency band; (iv) constructing a correlation matrix representative of the reflected signal, wherein the correlation matrix comprises a number of signal eigenvectors and a number of noise eigenvectors; (v) decorrelating the correlation matrix by dividing the reflected signal according to frequency sub-bands within the diagnostic frequency band, wherein adjacent bands of the frequency sub-bands overlap, forming a series of iterated correlation matrices using signal eigenvectors and noise eigenvectors from each of the overlapping frequency sub-bands, forming a decorrelated matrix by averaging the iterated correlation matrices, wherein the decorrelated matrix comprises a finite group of signal eigenvectors and a finite group of noise eigenvectors; and (vi) constructing a scattering signature of the target object from the finite group of signal eigenvectors, wherein the scattering signature is indicative of the properties of the embedded dielectric region and the adjacent dielectric region.

26 Claims, 6 Drawing Sheets

ELECTROMAGNETIC DETECTION OF AN EMBEDDED DIELECTRIC REGION WITHIN AN AMBIENT DIELECTRIC REGION

CROSS REFERENCE TO RELATED APPLICATIONS

This application claims the benefit of U.S. Provisional Application Ser. No. 60/068,983, MICROWAVE DETECTION SYSTEM FOR LOCATING HEMORRHAGE SITES WITHIN THE CRANIUM AND OTHER REGIONS, filed Dec. 29, 1997.

STATEMENT REGARDING FEDERALLY SPONSORED RESEARCH OR DEVELOPMENT

This invention was made with Government support under Contract Nos. DAMD17-96-C-6074 awarded by U.S. Army Medical Research and F08630-94-C0082 awarded by the U.S. Air Force. The Government has certain rights in the invention.

BACKGROUND OF THE INVENTION

The present invention relates to the use of electromagnetic radiation to enable the detection of the presence and nature of a region embedded within a test object.

The internal structure of an object may be analyzed by a number of conventional imaging systems. X-ray, MRI, and ultrasound systems are good examples. There are many challenges associated with imaging system design. Imaging systems must enable quick and efficient examination of the object and minimize data processing. Further, system components are preferably portable and physically adaptable to a diverse array of work environments.

In the medical field, for example, a major problem facing medical personnel in military and civilian emergency situations is the need to examine victims quickly, determine the patient's vital signs, diagnose and decide on the treatment alternatives. An important part of the process is location of internal bleeding. Traditional medical imaging systems such as X-ray CT, MRI, and ultrasound are not practical as the size and weight of such systems precludes their use on the battlefield or at accident sites. Extensive processing of the measured data reduces the timeliness of the diagnosis, and places the patient out of the sight of the physician for extended periods of time.

Accordingly, there is a need for an improved system for detecting and locating a dielectric region having a given permittivity embedded in an ambient region having a different permittivity.

BRIEF SUMMARY OF THE INVENTION

This need is met by the present invention wherein a method of and system for electromagnetically detecting an embedded dielectric region within a target object are provided.

In accordance with one embodiment of the present invention, a method of electromagnetically detecting an embedded dielectric region within a target object is provided comprising the steps of: (i) selecting a target object including a plurality of discrete scattering mediums, wherein the plurality of discrete scattering mediums include the embedded dielectric region and an adjacent dielectric region, and wherein the plurality of discrete scattering mediums define at least one dielectric interface between the embedded dielectric region and the adjacent dielectric region; (ii) directing electromagnetic radiation at the target object, wherein the electromagnetic radiation is characterized by a diagnostic frequency that is varied incrementally over a diagnostic frequency band; (iii) detecting electromagnetic radiation reflected by the target object over the predetermined frequency band such that there are M measurements of a reflected electromagnetic signal at frequencies $f_1$, $f_2$, ..., $f_N$, where M represents a number of scattering mediums within the target object and where N represents a number of diagnostic frequencies within the diagnostic frequency band; (iv) constructing a correlation matrix representative of the reflected signal, wherein the correlation matrix comprises a number of signal eigenvectors and a number of noise eigenvectors; (v) decorrelating the correlation matrix by dividing the reflected signal according to frequency sub-bands within the diagnostic frequency band, wherein adjacent bands of the frequency sub-bands overlap, forming a series of iterated correlation matrices using signal eigenvectors and noise eigenvectors from each of the overlapping frequency sub-bands, forming a decorrelated matrix by averaging the iterated correlation matrices, wherein the decorrelated matrix comprises a finite group of signal eigenvectors and a finite group of noise eigenvectors; and (vi) constructing a scattering signature of the target object from the finite group of signal eigenvectors, wherein the scattering signature is indicative of the properties of the embedded dielectric region and the adjacent dielectric region.

The step of constructing the scattering signature may incorporate the step of determining a frequency dependent scattering spectrum of selected ones of the discrete scattering mediums. The scattering signature may comprise a signal plot across the diagnostic frequency band. The reflected electromagnetic signal may comprise a real component and an imaginary component, and the scattering signature may comprise a plot of the real component or the imaginary component across the diagnostic frequency band. Alternatively, the scattering signature may comprise a plot of the amplitude or phase of the reflected electromagnetic signal across the diagnostic frequency band.

The method of the present invention may further comprise the step of substantially removing portions of the reflected signal corresponding to predetermined known scatterers, whereby signal portions of interest can be made to dominate the construction of the scattering signature. Portions of the reflected signal corresponding to predetermined known scatterers may be substantially removed by constraining the noise eigenvectors to be orthogonal to the signal eigenvectors of known scatterers. Portions of the reflected signal corresponding to background scatterers may also be removed.

The method of electromagnetically detecting an embedded dielectric region within a target object according to the present invention may further comprise the steps of estimating the number of signal eigenvectors within the reflected signal and verifying the number of signal eigenvectors within the reflected signal by plotting an eigenvalue spectrum of the correlation matrix and identifying a set of substantially equal eigenvalues.

Each frequency sub-band preferably differs from an adjacent frequency sub-band in that their respective frequency ranges are incremented relative to one another by an amount equal to the incremental variation of the diagnostic frequency. The diagnostic frequency band preferably extends from about 0.5 GHz to about 20.0 GHz, or, preferably from about 0.5 GHz to about 6.0 GHz.

In accordance with another embodiment of the present invention, a system for electromagnetically detecting an embedded dielectric region within a target object is provided comprising a target object, an electromagnetic radiation source and detector, and a data processor. The target object includes a plurality of discrete scattering mediums, wherein the plurality of discrete scattering mediums include the embedded dielectric region and an adjacent dielectric region, and wherein the plurality of discrete scattering mediums define at least one dielectric interface between the embedded dielectric region and the adjacent dielectric region. The electromagnetic radiation source is configured to direct electromagnetic radiation at the target object, wherein the electromagnetic radiation is characterized by a diagnostic frequency that is varied incrementally over a diagnostic frequency band. The electromagnetic radiation detector is configured to detect electromagnetic radiation reflected by the target object over the predetermined frequency band such that there are M measurements of a reflected electromagnetic signal at frequencies $f_1, f_2, \ldots, f_N$, where M represents a number of scattering mediums within the target object and where N represents a number of diagnostic frequencies within the diagnostic frequency band. The data processor configured to: (i) construct a correlation matrix representative of the reflected signal, wherein the correlation matrix comprises a number of signal eigenvectors and a number of noise eigenvectors; (ii) decorrelate the correlation matrix by dividing the reflected signal according to frequency sub-bands within the diagnostic frequency band, wherein adjacent bands of the frequency sub-bands overlap, forming a series of iterated correlation matrices using signal eigenvectors and noise eigenvectors from each of the overlapping frequency sub-bands, and forming a decorrelated matrix by averaging the iterated correlation matrices, wherein the decorrelated matrix comprises a finite group of signal eigenvectors and a finite group of noise eigenvectors; and (iii) construct a scattering signature of the target object from the finite group of signal eigenvectors, wherein the scattering signature is indicative of the properties of the embedded dielectric region and the adjacent dielectric region.

The system may further comprise a frequency spectrum plotter in communication with the data processor, wherein the data processor is operative to cause the frequency spectrum plotter to display the scattering signature as a frequency dependent scattering spectrum of selected ones of the discrete scattering mediums. The scattering signature preferably comprises a signal plot across the diagnostic frequency band.

The data processor may be further configured to substantially remove portions of the reflected signal corresponding to predetermined known scatterers, whereby signal portions of interest tend to dominate the construction of the scattering signature. The data processor may also be configured to substantially remove portions of the reflected signal corresponding to predetermined known scatterers by constraining the noise eigenvectors to be orthogonal to the signal eigenvectors of known scatterers. The data processor may additionally be configured to substantially remove the portions of the reflected signal corresponding to background scatterers.

The data processor may be further configured to input an estimate of the number of signal eigenvectors within the reflected signal and enable verification of the number of signal eigenvectors within the reflected signal by generating a plot of an eigenvalue spectrum of the correlation matrix. The data processor is preferably configured to select each frequency sub-band such that it differs from an adjacent frequency sub-band in that their respective frequency ranges are incremented relative to one another by an amount equal to the incremental variation of the diagnostic frequency.

Accordingly, it is an object of the present invention to provide an improved method of and system for electromagnetically detecting an embedded dielectric region within a target object. Other objects of the present invention will be apparent in light of the description of the invention embodied herein.

BRIEF DESCRIPTION OF THE SEVERAL VIEWS OF THE DRAWINGS

The following detailed description of the preferred embodiments of the present invention can be best understood when read in conjunction with the following drawings, where like structure is indicated with like reference numerals and in which.

DETAILED DESCRIPTION OF THE PREFERRED EMBODIMENTS

Figure 1:
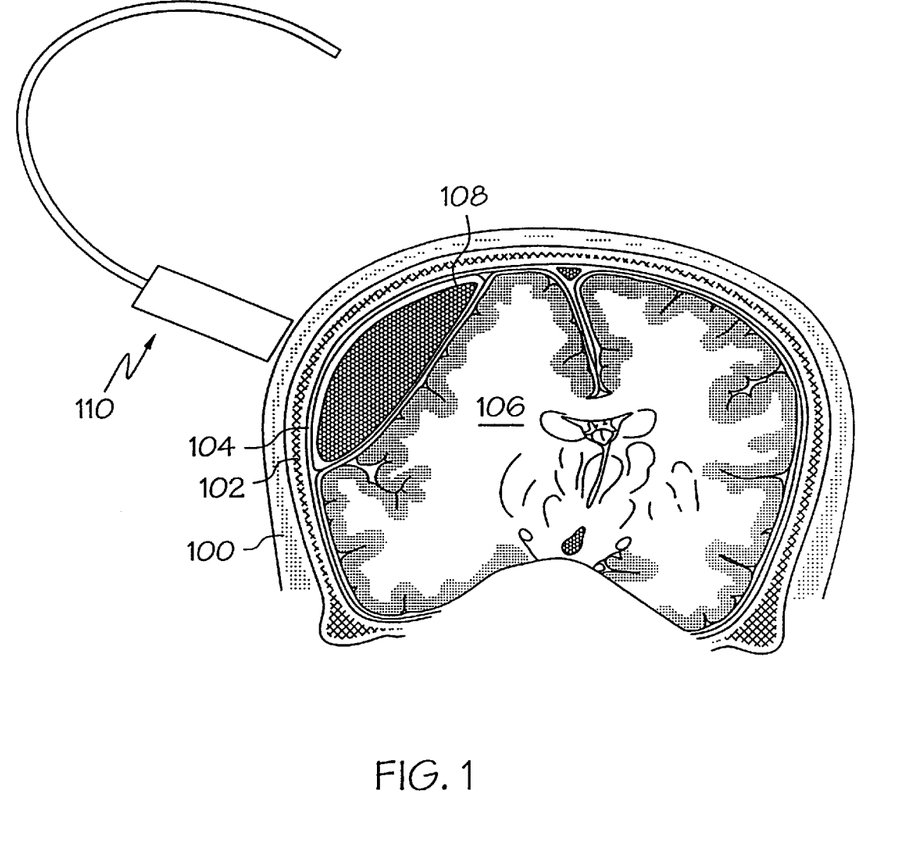
FIG. 1 is an illustration of an application of the system and method of the present invention.

Referring initially to FIG. 1, an application of the system and method of the present invention is illustrated. Dielectric scattering mediums present in the illustrated case are the skin 100, bone 102, and dura 104 that enclose the brain 106, and an embedded hematoma 108. An electromagnetic antenna 110 is indicated schematically. The parameter of interest in the detection system is the permittivity of the materials in the structure. The physical basis of the detection/location system is the scattering of electromagnetic waves by any objects located in the path of the wave. Electromagnetic scattering is a result of the fields satisfying the boundary conditions on the surface of the object. Similar boundary conditions on the fields are imposed at the interface between two dielectric media. Boundary conditions are defined for the fields as before, but the conditions are less restrictive since none of the fields are zero on the interface. Thus, fields exist on both sides of the interface, an incident field, a reflected field, and a transmitted field. The boundary conditions on the electric and magnetic fields at the interface will determine the field behavior in all regions.

The permittivity of various tissue types at 37° C. and illuminated at a frequency of 2450 MHz, the electrical constitutive parameters of blood and brain tissue are as shown in Table 1.

TABLE 1

Dielectric Properties of Brain and Blood at 2450 MHz

| Parameter | Brain (Gray Matter) | Blood |
|---|---|---|
| Permittivity | 43 | 60 |
| Conductivity | 1.43 | 2.04 |

It was noted earlier that the fundamental principle of operation involves the detection of the brain-blood interface. The most convenient way to discuss this idea is by defining a quantity that will quantify the discontinuity between two materials and characterize the interface. A logical choice is to form a ratio between the permittivities of the materials. Let the contrast ratio $\rho$, be defined as, $$\rho = \epsilon_{blood}/\epsilon_{brain},$$

where the larger permittivity is placed in the numerator to ensure that $\rho$ is greater than one. Contrast, as we have defined it, is a measure of the level of reflected signal one can expect from a dielectric discontinuity. Contrast ratio values that are much greater than one indicate the presence of interfaces that will give rise to large reflected signals that will be easily detected. Contrast values in the range, $1 \leq \rho \leq 2$ will also produce a backscattered signal, but the reflected signal magnitude will be smaller, negatively impacting the system signal to noise ratio (SNR).

Electromagnetic Signature. A backscattered or reflected electromagnetic signal is a measure of the reflecting properties of the object and is expressed through the reflection coefficient of the material, $\Gamma$. This is a complex quantity, in the mathematical sense, that can be related to the constitutive properties of the scatterer, $\epsilon$ and $\mu$. $\Gamma$ is directly related to the scattering parameter, $S_{11}$. Thus, by making a measurement of the reflection coefficient or scattering parameters, one can find indirectly the electromagnetic properties of the scatterer. If data are taken over a wide range of frequencies, $\epsilon$ and $\mu$ are also known over the same frequency range and this behavior can be catalogued.

Scattering is dominated by the geometric properties or "characteristic dimension" of the target, and by its composition. The behavior becoming one in which over a wide frequency band, the signature has a resonant behavior, with peaks at well-defined frequencies corresponding to characteristic dimensions on the target. Targets such as blood pools are many times not very well defined geometrical shapes, but have a relatively well defined composition.

Since the dielectric constant of most materials is frequency dependent, one should carefully choose the diagnostic operating frequency to optimize the detection performance of the present invention. Contrast values as small as $\rho=1.05$ can be detected using the signal processing algorithms of the present invention. The contrast ratio of the brain-blood discontinuity at a frequency of 2450 MHz is approximately 1.4, so one can expect to achieve good detection performance by interrogating at this frequency according to the present invention.

Signal processing. The signal processing technique of the present invention can be used to uniquely characterize embedded scatterers in target objects from a wide band electromagnetic signature. However, before we define a signature we will discuss radar cross section (RCS) and how it is obtained. RCS, $\sigma$, can most effectively be obtained by measurement. RCS, $\sigma$, is defined by:

$$\sigma = \lim_{R \to \infty}\left(4\pi R^2 \frac{|E^{scat}|^2}{|E^{inc}|^2}\right)$$

The scattered electric field must be measured or computed from the solution of Maxwell's equations. The limit is taken after the ratio of the scattered field magnitude squared and the incident field magnitude squared is multiplied by the factor $4\pi R^2$. This removes the range dependence making the RCS dependent upon the scatterer properties only.

If the object is a conductor, dependence is geometric, since the boundary condition is on the tangential electric field at the boundary. This was commonly the case until the advent of low observable technology which modified the structure of scatterers by adding materials to regions on the scatterer having high backscatter. This, in turn, has modified the boundary condition on the surface bringing into the problem the constitutive properties, $\epsilon$ and $\mu$, the permittivity and permeability, respectively. The boundary conditions now include these parameters and they can themselves be used as a signature of the object.

The backscattered signal is a measure of the reflecting properties of the object and is expressed through the reflection coefficient of the material, $\Gamma$. This is a complex quantity, in the mathematical sense, that can be related to the constitutive properties of the scatterer, $\epsilon$ and $\mu$. $\Gamma$ is also related to the scattering parameters, in fact, it is $S_{11}$. Thus, by making a measurement of the reflection coefficient or scattering parameters, one can, in principle, find the electromagnetic properties of the scatterer.

If data are taken over a wide range of frequencies, then $\epsilon$ and $\mu$ are also known over the same frequency range and this behavior can be catalogued. Any scatterer has two electromagnetic signatures associated with it, 1) a Radar Cross Section defined by the target geometry, and 2) a constitutive signature related to the target reflection characteristics, which in turn depend upon the target's constitutive properties.

Targets such as blood pools are many times not very well defined geometrical shapes, but have a well defined composition. Scattering is dominated by a "characteristic dimension" of the target. The behavior becoming one in which over a wide frequency band, the signature has a resonant behavior, with peaks at well-defined frequencies corresponding to characteristic dimensions on the target. A nonmetallic scatterer will also have a well-defined geometry, but the primary contributor to the backscatter is the constitutive properties of the target.

Auto-correlation Processing. According to the Wold decomposition, any signal can be written in the following form:

$$s=r+\eta,$$

where $r$ is the known signal and $\eta$ is a Gaussian noise. Signals of this form are central to Angle of Arrival (AOA) technology, which is frequently utilized in aircraft location and identification. AOA techniques are concerned with two challenges: spatial location of a signal source and signal identification. Since the sources of signals impinging on an aircraft are from radar, communications, and electronic warfare systems, and since such systems operate using known frequencies and modulations, the only major problem in the AOA context is spatial location. Spatial location can be accomplished using an array of receivers with known properties, located in a known pattern.

According to the present invention, a single antenna is utilized to transmit and receive electromagnetic signals.

Further, the system is operated over a wide band of frequencies by stepping the frequency of the electromagnetic source. It is contemplated by the present invention that the choice of frequency band will be dictated by the physics of the problem. For the hemorrhage detection problem, or medical detection, for example, the frequency band will be centered at a frequency that optimizes the desired response with minimal degradation as the band edges are approached from above or below. For hemorrhage detection, one would likely choose a frequency in the 0.5–2 GHz range to obtain the best possible tissue penetration. Using a high frequency such as X-band would be suitable for surface detection, but would have limited, if any, brain penetration. Thus, the physics of the problem will drive the selection of the operating parameters for the system.

Auto-correlation of Continuous Signals. Auto-correlation for a continuous function is defined by the following expression, $$R(\tau) = \int_{-\infty}^{\infty} f(x)f(x-\tau)\,dx,$$

This is a measure of the "closeness" of the function and a shifted version of itself. The result is a function of the parameter $\tau$. The function is typically real valued since one would like to have some ability to compare two values of $R(\tau)$ and if the quantity is not real such comparisons cannot be made. Auto-correlation can be defined for complex valued functions as:

$$R(\tau) = \int_{-\infty}^{\infty} f^*(x)f(x-\tau)\,dx,$$

The frequency domain properties of f are desired, hence the Fourier transform can be taken. It is of some interest to take the transform of $R(\tau)$ and consider this result. Taking this we obtain:

$$\mathcal{F}[R(\tau)] = \int_{-\infty}^{\infty} R(\tau)e^{j\omega\tau}\,d\tau = |F(\omega)|^2, \text{ where,}$$

$F(\omega)$ is the Fourier transform of the function f. This is "the power in the function f." This can be seen if we consider the function as a voltage and the voltage be assumed to exist on a 1$\Omega$ resistor.

Auto-correlation of Stepped Frequency Signals. Suppose we have a situation where we have M scatterers and illuminate this constellation with a source having a signal that is of the form:

$$s(\omega) = e^{j\left(\frac{\omega}{c}\right)x}.$$

Let the radian frequency be $2\pi f$, and the resulting signal is:

$$s(\omega) = e^{j\left(\frac{2\pi f}{c}\right)x} = e^{j2\pi f\left(\frac{x}{c}\right)} = e^{j2\pi f t}.$$

Letting the frequency become discrete leads to a set of frequencies that are used to interrogate the terrain, $\{f_1, f_2, \ldots, f_M\}$. Each frequency is permitted to exist for a finite duration during which the target region is illuminated. The signal repeats every T seconds, and is of $\tau$ seconds in duration. This can be thought of as a set of individual signals, each a CW signal having time harmonic dependence. These signals are used to illuminate the terrain and the return is received and processed.

The reflected signal from the $l^{th}$ scatterer is given by:

$$s_l(\omega) = \Gamma_l e^{j\left(\frac{\omega}{c}\right)x_l} = \Gamma_l e^{j2\pi f t_l},$$

Where f, is the cyclic frequency, and $t_l$, is the two-way travel time from the source to the $l^{th}$ scatterer and back, and $\Gamma_l$ is the reflection coefficient for the $l^{th}$ scatterer. The total signal is the vector sum of the M reflected signals from the scatterers in the illuminated region. This is just, $$s_T(\omega) = \sum_{l=1}^{M} s_l(\omega) = \sum_{l=1}^{M} \Gamma_l e^{j2\pi f t_l}$$

We know that there will be additive noise present in the system and this will be frequency dependent also. This will modify the form above to, $$s_T(f) = \sum_{l=1}^{M} \Gamma_l e^{j2\pi f t_l} + \eta(f)$$

This then is the signal with which the system will have to work.

Auto-Correlation of Discrete Frequency Signals. Since the signal is composed of desired and undesired components, we need to have some method of separating these out. A single frequency measurement cannot determine the desired information, more data must be obtained. The spatial measurement uses all of the antennas in the array to increase the information content in the measurement. The extension to the frequency domain case will require that one take data over N frequencies, and then perform some operation on this data to determine scatterer location. The resulting data will be of the form:

$$s_T(f_m) = \sum_{l=1}^{M} \Gamma_l e^{j2\pi f_m t_l} + \eta(f_m)$$

This equation is true for m=1,2,3 . . . , N, and leads to the following set of equations:

$$s_T(f_1) = \sum_{l=1}^{M} \Gamma_l e^{2\pi j f_1 t_l} + \eta(f_1)$$

$$s_T(f_2) = \sum_{l=1}^{M} \Gamma_l e^{2\pi j f_2 t_l} + \eta(f_2)$$

$$\vdots$$

$$s_T(f_N) = \sum_{l=1}^{M} \Gamma_l e^{2\pi j f_N t_l} + \eta(f_N)$$

This is a set of N equations in M unknowns, and the ability to obtain the solution will depend on the relationship between N and M. The system can be written in a matrix form by noting that the left hand side of the equation is a column vector and that the right hand side is the sum of a vector-matrix product (a column vector) and another column vector. This is conveniently written as:

$$\bar{s}_T = \overline{P\Gamma} + \bar{\eta},$$

where matrix notation has been used to compress the space on the page. How the data is processed is the next question that must be answered. Since we are receiving the signals from a number of discrete sources, we would like some means of separating the various contributions. One method of accomplishing this is to investigate the auto-correlation of the backscattered signal. The resulting matrix will have an eigen-structure that will permit the desired information to be obtained. The next section will discuss the specialized algorithm of the present invention that is utilized to obtain the desired signal information.

The Algorithm. We use multiple frequencies and measure the signal reflected from the test object. Let there be M measurements made of the reflected signal, at the frequencies, $\{f_1, f_2, \ldots, f_M\}$. The auto-correlation matrix, also referred to herein as the correlation matrix, is given by the following expression, $$\overline{\overline{C}} = E(\overline{s}_T \overline{s}_T^H),$$

where, $\overline{s}_T = \overline{\overline{P}}\,\overline{\Gamma} + \overline{\eta}$, and all quantities are as previously defined. This can be expanded using the definition of the total signal:

$$\overline{\overline{C}} = E(\overline{s}_d \overline{s}_d^H) + E(\eta \eta^H),$$

We have let the decomposition of the signal be in the form:

$$\overline{s}_d = \overline{\overline{P}}\,\overline{\Gamma},$$

is the matrix contains the array properties, and the vector is the scattering properties of the various interfaces. The second term is the noise auto-correlation and can be treated, for the case of Gaussian noise, as a constant, $\sigma_0^2$. Thus we can write, $$\overline{\overline{C}} = E\left(\overline{\overline{P}}\,\overline{\Gamma}\,\overline{\Gamma}^H \overline{\overline{P}}^H\right) + \sigma_0^2 \overline{\overline{I}},$$

where, $$\overline{\overline{C}}\overline{s}_d = E\left(\overline{\overline{P}}\,\overline{\Gamma}\,\overline{\Gamma}^H \overline{\overline{P}}^H\right)\overline{s}_d + \sigma_0^2 \overline{\overline{I}}\,\overline{s}_d$$

Since the vector $\overline{s}_d$ is written in the following way: $\overline{s}_d = \overline{\overline{P}}\,\overline{\Gamma}$, using this in the equation above will yield:

$$\overline{\overline{C}}\overline{s}_d = E\left(\overline{\overline{P}}\,\overline{\Gamma}\,\overline{\Gamma}^H \overline{\overline{P}}^H\right)\overline{\overline{P}}\,\overline{\Gamma} + \sigma_0^2 \overline{\overline{I}}\,\overline{s}_d$$

$$\overline{\overline{C}}\overline{s}_d = E\left[\overline{\overline{P}}\,\overline{\Gamma}(\overline{\Gamma}^H \overline{\Gamma})(\overline{\overline{P}}^H \overline{\overline{P}})\right] + \sigma_0^2 \overline{\overline{I}}\,\overline{s}_d$$

$$\overline{\overline{C}}\overline{s}_d = E\left[(\overline{\Gamma}^H \overline{\Gamma})(\overline{\overline{P}}^H \overline{\overline{P}})\overline{\overline{P}}\,\overline{\Gamma}\right] + \sigma_0^2 \overline{\overline{I}}\,\overline{s}_d$$

$$\overline{\overline{C}}\overline{s}_d = E\left[(\overline{\Gamma}^H \overline{\Gamma})(\overline{\overline{P}}^H \overline{\overline{P}})\right]\overline{\overline{I}}\,\overline{s}_d + \sigma_0^2 \overline{\overline{I}}\,\overline{s}_d$$

$$\overline{\overline{C}}\overline{s}_d = \left[E\left((\overline{\Gamma}^H \overline{\Gamma})(\overline{\overline{P}}^H \overline{\overline{P}})\right) + \sigma_0^2\right]\overline{s}_d = \lambda_C \overline{s}_d$$

This is a statement of the eigenvalue problem, a solution to which is easily obtained. The matrix $\overline{\overline{C}}$ has dimension M, thus if the matrix has full rank it will have M eigenvectors and eigenvalues. If it is not of full rank, then there will be some number of degenerate eigenvectors. A member of the set of degenerate eigenvectors has the same eigenvalue as the other members of the set. One can see that the smallest value that $\lambda_C$ takes on is when the first term in brackets is zero. Thus, we have a set of eigenvectors having as their eigenvalue, $\sigma_0^2$. These are the noise eigenvectors of the measured signal.

Figure 2:
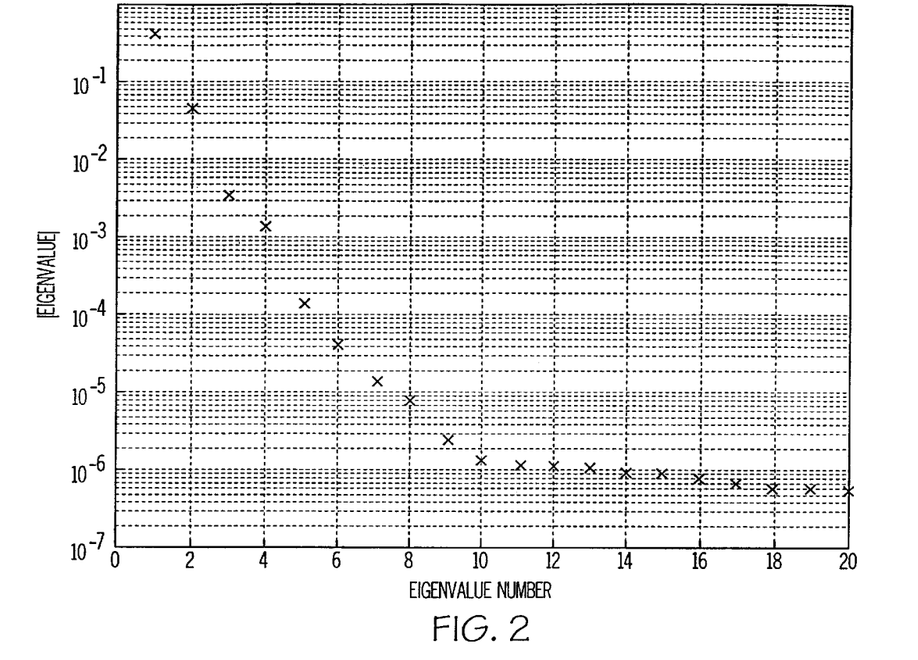
FIG. 2 is an illustration of an eigenvalue spectrum according to the present invention.

If there are N signals then there will be N signal eigenvectors if the individual signals are uncorrelated and thus M-N noise eigenvectors. Since a priori knowledge of the actual number of signals in a measurement is not necessarily a known in advance, one can make an educated guess as to the number and then test the quality of the guess by plotting the eigenvalue spectrum. A typical eigenvalue spectrum is shown in FIG. 2. The spectrum clearly shows signal eigenvalues monotonically decreasing, followed by a set of noise eigenvalues that are nearly constant.

Decorrelation Technique. Signals used in the interrogation of a region are a sequence of single frequencies with known amplitude and phase relationships. At a frequency f signals are of the form, $$s(f) = \Gamma_1 e^{j2\pi f l_1} + \ldots + \Gamma_M e^{j2\pi f l_M} + \eta(f).$$

Data are gathered at a number of frequencies and the resulting system of received signals is used to form the correlation matrix. If the signals (frequencies) are uncorrelated then one obtains the previous results and a distinct decomposition into orthogonal noise and signal subspaces. This procedure is also valid if the signals are partially correlated, the only real difficulty occurs if there is perfect correlation between the signals. Since the signal source for our interrogation is the swept source of the vector network analyzer, coherence of the signals is a problem and one must apply the methods of the present invention to achieve improved algorithm performance.

Algorithm performance is greatly improved if the signals are more nearly uncorrelated than for correlated cases. Hence a method has been developed to decorrelate the signals. This method we refer to as "averaging" and is an integral part of the signal processing algorithm set. As is described below, the algorithm sub-divides the measurement band into sub-bands and processes each sub-band. The technique can be best understood by considering a special case having a limited number of frequencies and scatterers. This will enable those practicing the present invention to better understand the process and its importance.

Let the interrogated region contain two scatterers characterized by their respective reflection coefficients, $\Gamma_1$, and $\Gamma_2$. Let data be taken at four frequencies, $f_1, f_2, f_3, f_4$. One can view the data taken at the various frequencies as being taken over an array of antennas. The arrays are defined by the user and for this example, one can write:

$$r_1 = \sum_{l=1}^{2} \Gamma_l e^{2\pi j f_1 t_l} + \eta(f_1)$$

$$r_2 = \sum_{l=1}^{2} \Gamma_l e^{2\pi j f_2 t_l} + \eta(f_2)$$

$$\vdots$$

$$r_4 = \sum_{l=1}^{2} \Gamma_l e^{2\pi j f_4 t_l} + \eta(f_4)$$

Figure 3:
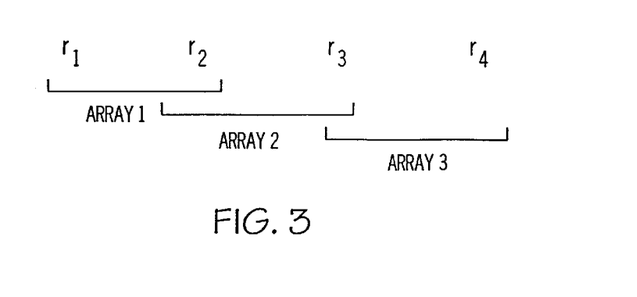
FIG. 3 illustrates a set of arrays that can be used for signal processing according to the present invention.

These relations, each defining a received signal in the frequency domain, can be written in matrix-vector form as:

$$\bar{s} = \overline{\overline{A}}\Gamma + \bar{\eta},$$

where the quantities are as defined before. This form for the signal is representative of the entire data set, processed to find the eigenstructure. One can use this very simple case to illustrate the application of the decorrelation scheme. FIG. 3 illustrates a set of arrays that can be used for processing.

We assume the existence of received data $r_k$ at four frequencies and form an overlapped set of subsets of the signals. Let array 1 be defined by:

$$\bar{r}_1 = \begin{bmatrix} r_1 \\ r_2 \end{bmatrix}, \text{where,}$$

$$r_1 = \sum_{l=1}^{2} \Gamma_l e^{2\pi j f_1 t_l} + \eta(f_1)$$

$$r_2 = \sum_{l=1}^{2} \Gamma_l e^{2\pi j f_2 t_l} + \eta(f_2),$$

This will permit us to write the above in the following compact form:

$$\bar{r}_1 = \overline{\overline{A}}\Gamma + \bar{\eta}$$

Prior to further discussion, let us consider some results from matrix algebra. Let there be defined two matrices, $\overline{\overline{A}}$, and $\overline{\overline{D}}$. These are defined in the following way:

$$\overline{\overline{A}} = \begin{bmatrix} a & b \\ c & d \end{bmatrix}, \text{ and } \overline{\overline{D}} = \begin{bmatrix} \alpha & 0 \\ 0 & \beta \end{bmatrix}.$$

We will encounter products involving these two matrices in the course of this work. Consider forming powers of $\overline{\overline{D}}$, e.g. $\overline{\overline{D}}^N$. Using matrix multiplication and induction on the exponent, we can prove that, $$\overline{\overline{D}}^N = \begin{bmatrix} \alpha^N & 0 \\ 0 & \beta^N \end{bmatrix}.$$

Next consider the product, $\overline{\overline{A}}\, \overline{\overline{D}}$. This is just:

$$\overline{\overline{AD}} = \begin{bmatrix} \alpha a & \beta b \\ \alpha c & \beta d \end{bmatrix}.$$

This will enable us to write the products in terms that are formed in the development of the correlation matrix in a much simpler form. With these useful relationships the data will be processed as arrays, which has the effect of taking a moving average through the data. This process will remove many of the "small" signals that appear in the correlation matrix, leaving only the most important signals.

The other arrays are defined in a similar fashion, except that for the remainder of the arrays we must include a another matrix D, defined as:

$$\overline{\overline{D}} = \begin{bmatrix} e^{-2\pi j \Delta f t_1} & 0 \\ 0 & e^{-2\pi j \Delta f t_2} \end{bmatrix}, \text{where,}$$

$\Delta f$ is the frequency increment in the measurement system. This happens because each array is taken over a set of frequencies that differ by a one frequency increment. The result for the $k^{th}$ array is:

$$\bar{r}_k = \overline{\overline{AD}}^{k-1}\Gamma + \bar{\eta}.$$

An iterated correlation matrix is formed using each of the vectors from the sub-bands. This leads to the following result for the $k^{th}$ correlation matrix, $R_k$.

$$R_k = E\left[\overline{\overline{AD}}^{k-1}(\Gamma\Gamma^H)\overline{\overline{D}}^{k-1H}\overline{\overline{A}}^H\right] + \sigma^2 \bar{\bar{I}},$$

where,
E denotes the expectation operator, and the superscript H denotes the hermitian conjugate of the matrix. The final step is to form the average of the various correlation matrices, the result is:

$$R_{avg} = \frac{1}{M}\sum_{k=1}^{M} R_k.$$

This is used to decorrelate the received signals removing the effects of coherence and producing a new decorrelated or localized correlation matrix with an eigenstructure having the most well-defined signal and noise subspaces. There being a finite group of signal eigenvectors, and a second finite group of noise eigenvectors. The technique also assumes a reasonable guess at the number of signals is available. This will require skill on the part of the user to estimate the number of signals so as not to overwhelm himself with the interpretation of the results.

Determination of Scatterer Frequency Dependence. Scattering by a dielectric is dependent upon the properties of the medium in which the wave is propagating and on the material with which the wave interacts. The situation is such that a wave impinges upon an interface and to satisfy the boundary conditions, a reflected wave is set up. The remainder is transmitted into the second material. The reflected wave is characterized by the coefficient $\Gamma$, the reflection coefficient. This coefficient is in general, complex and thus the amplitude of the reflection coefficient is the quantity of concern. The value of the reflection coefficient depends upon the wave impedance in each material. This dependence is, $$\Gamma = \frac{Z_1 - Z_0}{Z_1 + Z_0}.$$

The wave impedance in turn, depends upon the constitutive parameters of the materials. i.e.

$$Z_k = \sqrt{\frac{\mu_k}{\varepsilon_k}}.$$

This dependence is the basis for the constitutive signature of biological materials. There is a second signature that is of importance, the geometrical signature. This characterizes the geometry of the interface and is used in imaging of the interface. The geometry of the interface can be simple or quite complex. The ability to locate the interface and find its signature is fundamental to the system of the present invention.

We now consider the procedure for the determination of the scattering amplitude response at the $p^{th}$ frequency of the $k^{th}$ scatterer, $\Gamma_k(f_p)$, k=1, 2, . . . L. Towards this end we consider a band of frequencies of width $B_r$ and centered at $f_p$. Let there be (N+1) samples of data over this band. The signal model corresponding to this band of frequencies is given by, $$r_l = r(f_l) = \sum_{k=1}^{L} \Gamma_k(f_l) e^{-j2\pi f_l t_k}, l = p - N/2, \ldots, p + N/2.$$

Note that the scattering amplitudes are not assumed to be constant, and that the round trip time delays are assumed known and replaced by their estimates, $t_k$, previously determined. We assume a functional form for the $k^{th}$ scattering amplitude function $\Gamma_k(f)$. These functional forms may be different for different values of k. For instance, it may be a polynomial of order q, as given by, $$\Gamma_k(f) = \Gamma_{k0} + \Gamma_{k1}f + \Gamma_{k2}f^2 + \ldots + \Gamma_{kq}f^q.$$

Another possible functional form is a simple power rule:

$$\Gamma_k(f) = \Gamma_{k0}f^n.$$

As will be appreciated by those practicing the present invention, scattering data for certain biological materials have been measured over selected frequency ranges and the results are readily available. Such data has indicated that the dielectric properties are monotonically decreasing functions of frequency, e.g. $\epsilon(f) = \alpha f^{-m}$. Since the reflection coefficient depends on the media involved in the scattering, we can use this a priori information to our advantage.

All the results presented in this report assume a polynomial functional form, and the order of the polynomial could be different for different values of k. The problem of obtaining the dispersion characteristics for the target may now be formulated as the determination of parameters $\Gamma_{kl}$, k=1,2, . . . L and (=0,1,2 . . . q, that results in the best match between the measured data and the signal model in a least squares sense.

Details of the formulation are best explained by considering a particular case with L=2 and q=1. The formulation may then be generalized for arbitrary L and q. For this case, the functional forms for $\Gamma_1(f)$ and $\Gamma_2(f)$ are given by, $$r_o = (\Gamma_{10} + \Gamma_{11}f_0)e^{-j2\pi f_0 t_1} + (\Gamma_{20} + \Gamma_{21}f_0)e^{-j2\pi f_0 t_1} + \varepsilon_0$$

$$\vdots$$

$$r_N = (\Gamma_{10} + \Gamma_{11}f_0)e^{-j2\pi f_N t_1} + (\Gamma_{20} + \Gamma_{21}f_N)e^{-j2\pi f_N t_1} + \varepsilon_N.$$

The signal model, then, is given by, $$r_o = (\Gamma_{10} + \Gamma_{11}f_0)e^{-j2\pi f_0 t_1} + (\Gamma_{20}\Gamma_{21}f_0)ej2\pi f^{0t_2} + \epsilon_0$$

$$r_N = (\Gamma_{10} + \Gamma_{11}f_0)e^{-j2\pi f_N t_1} + (\Gamma_{20} + \Gamma_{21}f_N)e^{-j2\pi f_N t_2} + \epsilon_N.$$

Note that, for notational convenience, the frequencies $f_l$, l=p−N/2 to p+N/2 are renumbered from $f_0$ to $f_N$. The $\epsilon_k$ here represent the modeling errors. The measured signal at the $k^{th}$ frequency, $r_k$, may be expressed, compactly, as, $$r_k = \vec{W}_k^H \overline{\Gamma} + \epsilon_k, k=0,1, \ldots, N$$

where, $$\overline{\Gamma} = [\Gamma_{10}\Gamma_{11}\Gamma_{20}\Gamma_{<}]^T$$

$$W_k^H = [W_{k1}^H W_{k2}^H], k=0,1, \ldots \overline{N}$$

$$W_{kj}^H = [e^{-2\pi f_k t_j}], j=1,2.$$

The measurement vector, $\overline{r} = [r_0 \, r_1 \, \ldots \, r_{\overline{N}}]^T$ may now be expressed as the sum of a matrix-vector product and an error term as, $$\overline{r} = \overline{W}^H \overline{\Gamma} + \vec{\epsilon},$$

where, $$\overline{W} = [W_0 \, W_1 \, \ldots \, W_N],$$

and $$\overline{\epsilon} = [\epsilon_0, \epsilon_1, \ldots, \epsilon_N]^H$$

Our results continue to be valid for the L scattering centers and the $\Gamma_k(f)$ assumed to be represented by $q^{th}$ order polynomials, with, $$\vec{W}_k^T = [\vec{W}_{k1}^T \, \vec{W}_{k2}^T \, \ldots \, \vec{W}_{kL}^T]$$

$$\vec{W}_{kj}^T = [e^{-j2\pi f_k t_j} \ldots f_k^q e^{-j2\pi f_k t_j}], j=1,2, \ldots, L$$

$$\overline{\Gamma} = [\Gamma_{10} \ldots \Gamma_{1q}, \Gamma_{20} \ldots \Gamma_{2q}, \ldots, \Gamma_{L0} \ldots \Gamma_{Lq}]^T.$$

The optimum parameter vector $\overline{\Gamma}_{opt}$ may now be determined by requiring the error power $J = \|\vec{\epsilon}\|^2$ to be the least possible. Then, $$J = \overline{\epsilon}^H \overline{\epsilon} = \left(\overline{r} - \overline{W}^H \Gamma\right)^H \left(\overline{r} - \overline{W}^H \Gamma\right) = \overline{r}^H \overline{r} - \overline{r}^H \overline{W}^H \Gamma - \Gamma^H \overline{W} \overline{r} + \Gamma^H \overline{W} \overline{W}^H \Gamma$$

Taking the gradient of the error power, J, with respect to $\overline{\Gamma}$ and setting the result to zero yields, $$\nabla_\Gamma J = -\overline{W}\Gamma + \overline{W}\overline{W}^H \Gamma = 0$$

Therefore, the optimum parameter vector, $\overline{\Gamma}_{opt}$ is given by, $$\Gamma_{opt} = \left(\overline{W}\overline{W}^H\right)^{-1} \overline{W}\overline{\Gamma}$$

Once this parameter vector is defined, the amplitude frequency responses evaluated at $\Gamma_k(f_p)$, k=1,2, . . . , L, are readily determined. The frequency, then, is incremented from $f_p$ to $f_p + \Delta f$ and the procedure is repeated to determine the frequency response at this new frequency. The frequency response over the entire band may be determined in this fashion, except for small bands of width $B_r/2$ at the edges of the band. Considerations for the proper choice of $B_r$ and other parameters are discussed in the following paragraph.

The results obtained depend upon the choices made for the regression bandwidth, $B_r$, the frequency increment, $\Delta f$, and the number of subapertures, M, used to decorrelate $\overline{\overline{R}}$. The condition number of $(\overline{\overline{W}}\,\overline{\overline{W}}^H)$ depends upon $B_r$. The condition number, defined as the ratio of the largest eigenvalue to the smallest eigenvalue, is high if $B_r$ is too small and the system becomes ill-conditioned resulting in degraded estimates of scattering center frequency responses. The regression bandwidth corresponding to the first minimum of $B_r$ as a function of the condition number of $(\overline{\overline{W}}\,\overline{\overline{W}}^H)$ is the optimal choice. The choice of $\Delta f$ determines the rate of sampling of the scattered fields in the frequency domain and as such dictates the range of time delays that are not aliased. The $\Delta f$ must be chosen so that the expected range of time delays corresponding to the scattering centers on the target lie between $-\frac{1}{2}\Delta f$ and $\frac{1}{2}\Delta f$. Our results indicate that choosing the number of sub-apertures, M to be greater than one-half of the number frequency data points processed, decorrelates $\overline{\overline{R}}$ to a sufficient extent to permit the most significant scatterers to be located.

Additional Signal Processing Techniques. There are several techniques available to remove known scatterers from the problem, and these have proven to be very effective in producing results. We have identified one technique, background subtraction that can remove known scatterers leaving only signals of interest. A second technique, known as peak or scatterer subtraction, can be used to remove selected signals from the received signal data. A third technique comprises application of a constrained algorithm.

Background subtraction enables us to remove the contribution of scatterers that are in known locations. This technique dramatically increases the dynamic range of the measurement. Background subtraction is accomplished in two steps. First, a measurement is made of the set-up without the target present. As noted, the data collected contains amplitude and phase information for the region without the target present, primarily the response of the absorbing material. These data are stored on floppy disk and the target is placed on the absorber and the data taken and stored. Once this is completed, the difference is taken, and the difference data are processed. This removes "most" of the contribution from the background.

We assume the received signal is composed of a linear combination of scattering interfaces, M, in number, and a Gaussian noise contribution. The signal contains amplitude and phase information, stated mathematically, $$s_{BKGD}(f) = \sum_{m=1}^{M} a_m(f) e^{jk_m d_m} + \eta_{BKGD}(f),$$

where the amplitudes are $a_m$, the propagation constant in each region is $k_m$, the distance to the scatterer is $d_m$, and $\eta_{BKGD}(f)$ is a Gaussian noise at frequency f. The amplitude and phase data are stored. The data from the target and background are:

$$s_{BKGD+TGT}(f) = \sum_{m=1}^{M} a_m(f) e^{jk_m d_m} + \eta'_{BKGD}(f) + \sum_{l=1}^{P} t_l(f) e^{jk_l d_l} + \eta_{TGT}(f),$$

where the amplitudes of the P scatterers are denoted as $t_l$, the propagation constants and locations follow the same notation as before. The difference between these expressions is taken and the result is:

$$s_{TGT}(f) = s_{BKGD+TGT}(f) - s_{BKGD}(f)$$

$$= \sum_{l=1}^{P} t_l(f) e^{jk_l d_l} + \eta_{TGT}(f) + \eta'_{BKGD}(f) - \eta_{BKGD}(f).$$

Processing the data in the above expression produces the locations of the scatterers. Note that the noise term is composed of three contributions and it is this that leads to the statement that "most" of the background is removed. There can be slight configuration differences between measurements and this will preclude the complete removal of the background. Even with this, the success of background subtraction has been remarkable.

There are other methods for removing scatterers known to exist a priori in the region of interest. These scatterers can be removed using the subtraction method or by a constrained version of the algorithms that proceeds using Lagrange multipliers and optimizing a functional subject to a set of constraints as discussed previously. These are usually used to remove fixed scatterers from the problem. The background subtraction technique has been investigated for this application in a limited manner during Phase I and the results illustrate a dramatic improvement in algorithm performance.

Scatterer or peak subtraction is performed after the scatterers in the region have been located. After the location processing, the frequency dependence of the individual scatterers is determined. As is noted previously, there are scatterers in the region that are known a priori. These can cause confusion in the algorithm leading to false alarms. As is noted herein, the total received signal is composed of all target signals in the region that meet a user defined selection criterion. Suppose that the processing finds M scatterers. This would imply the signal has the form:

$$s_{proc}(f) = \sum_{s=1}^{M} A_s e^{jkd_s} + \eta(f)$$

The amplitudes $A_s$ have a known frequency dependence (determined by processing) and the phase terms are also known, hence, the contribution from undesired scatterers can be removed simply by subtraction of the known contributions. The resulting signal can be processed a second time and additional information can be obtained. This process is used to better locate desired targets and to obtain better approximations to the received signal.

The specialized algorithm of the present invention essentially separates the data space into the noise subspace and the signal subspace and searches the for those time delays steering vectors corresponding to which are orthogonal or nearly orthogonal to the noise subspace. The effect of sources at known locations may be reduced by introducing constraints into the algorithm. Let us define the space of all the steering vectors corresponding to the time delays of known sources as:

$$C = [c_1, c_2, c_3, \ldots c_P],$$

where $c_i$ are steering vectors corresponding to known sources. The noise subspace is now constrained to be orthogonal to C. This is accomplished by recognizing that the projection of the column space of X, the data space, into the orthogonal complement of the constraint space C, result in the projected columns of X being orthogonal to the noise subspace. The modified data space is now given by, $$\hat{X}X - P_C X.$$

$$P_C = C(C^H C)^{-1} C^H$$

Figure 9:
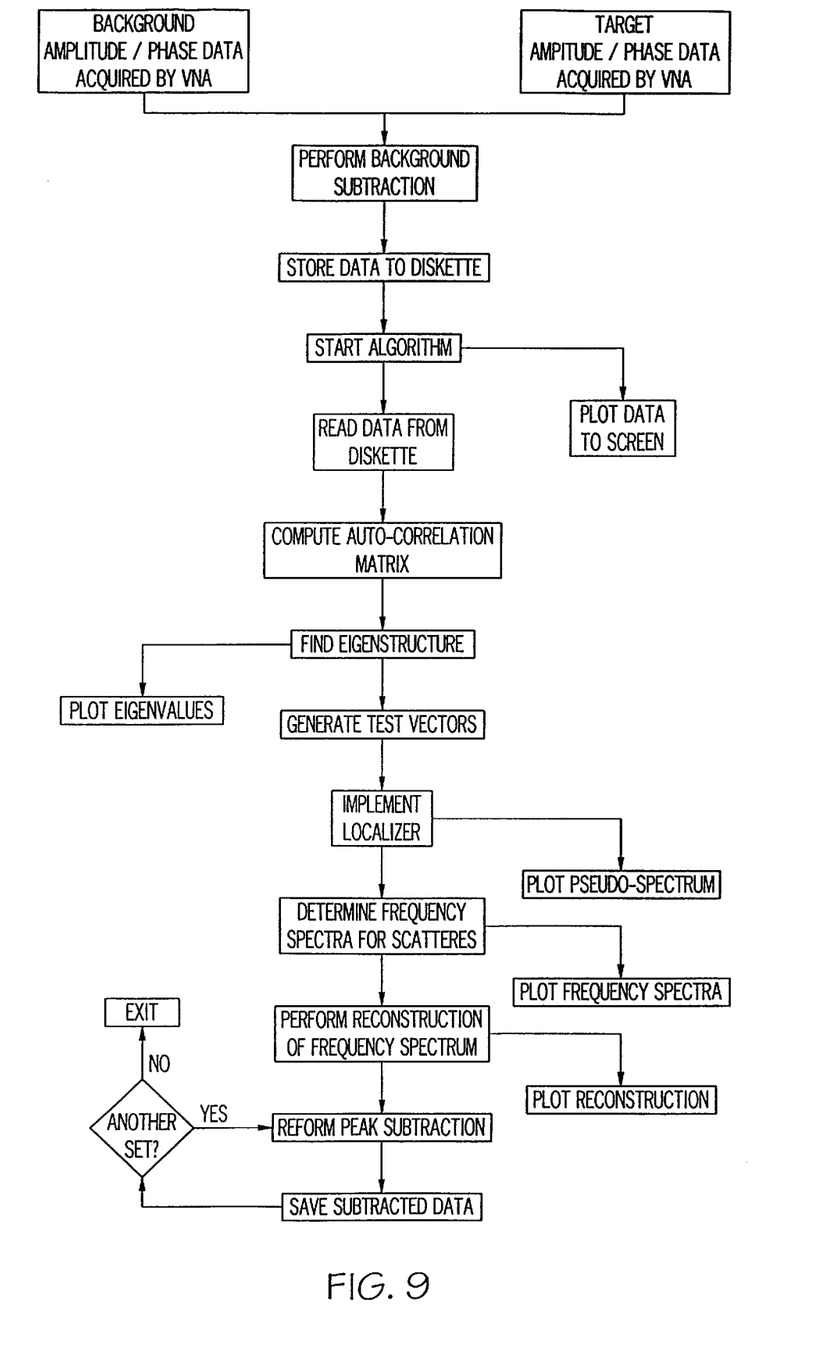
FIG. 9 is a flow chart illustrating the processes of the present invention.

The specialized algorithm of the present invention carried out with this modified data space which incorporates the known source locations will enhance the estimation of the unknown signal information. A flow chart illustrating the processes of the present invention is presented in FIG. 9.

Figure 4:
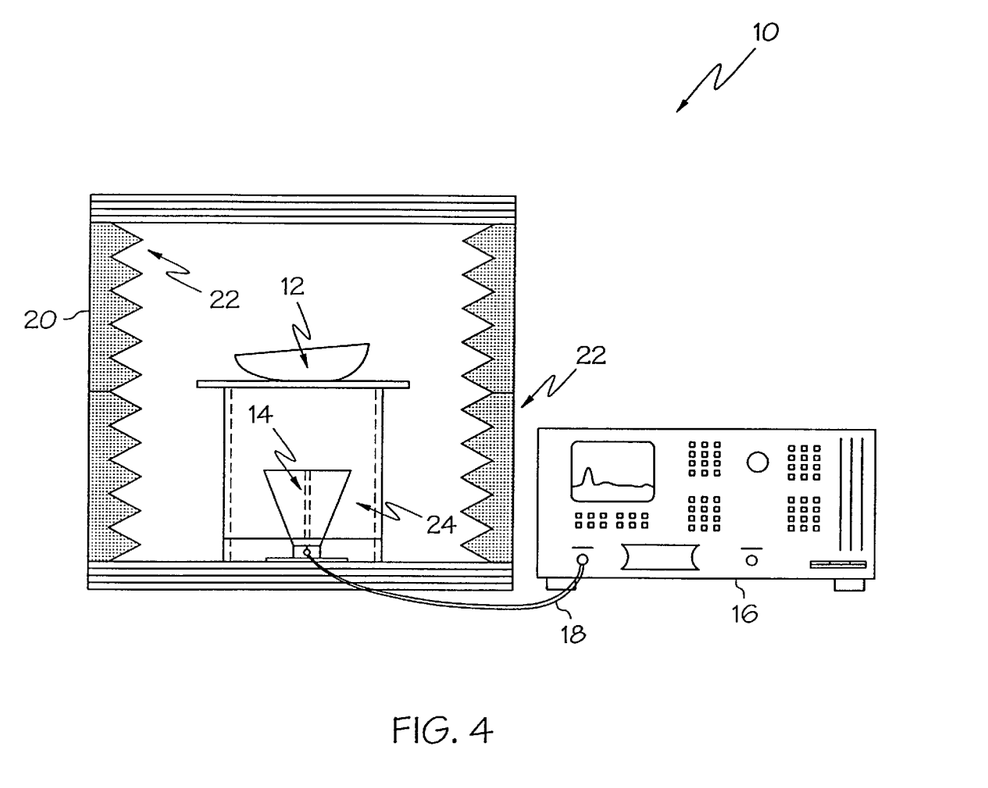
FIG. 4 illustrates a typical setup of a system of the present invention.

Test Setup. FIG. 4 illustrates a typical setup of a system of the present invention. The system 10 comprises, a target 12, an antenna 14 coupled to a signal source 16 via a coaxial cable 18, and an enclosure 20 lined with an electromagnetic absorber 22. Measurements are made by exciting the target 12 over a wide band of frequencies, and recording the backscattered signal. A signal source suitable for use in the present invention comprises a Vector Network Analyzer (VNA) and calibration set, available from Auritsu-Wiltron, Pine Brook, N.J., product model nos. 37247B and 3650 SMA. The antenna 14 may be a double ridged electromagnetic horn offering approximately 10 dB gain over the operating band. Available output power from the VNA is limited to 0 dBm, or 1 milliwatt.

The target 12 is supported by a Styrofoam stand 24 having a flat base upon which the target 12 rests. The target 12 is illuminated by the wideband antenna 14 (operating range about 2–20 GHz). The antenna 14 rests on a sheet of flat absorber 26, and the target 12 is illuminated from below, simulating a coronal interrogation. The reflected signals are received and the signal source records the amplitude and phase of each signal. The data is stored for further processing.

Measurements are made in several steps. For the purposes of better data presentation, all of the spectral results are normalized to those of a metal plate located at the resting point of the target. The first measurement made is to determine the background for background subtraction. Next, the reference is taken using a 8 inch square aluminum panel. Finally, the target 12 is placed on the support 22 and interrogated. This process, in the current configuration, takes approximately 2 minutes, the greatest part of the time spent in data transfer and storage. Once the data is available, it can be processed using any PC having MATLAB (available from the Math Works, Inc., Natick, Mass. All processing of the data occurs in a single MATLAB m-file, including graphical output of the data.

Measurement Results for Porcine Brain. Measurements were made for a chemically fixed porcine brain placed against a human skull section to simulate the actual conditions under which the instrument would be used. The skull section was placed on the support as a bowl and two brains were placed into the bowl with minimal separation between the skull surface and the brain. The reflected signal was measured and processed to determine the interface signature. FIGS. 5–8 present the signature of the skull interface backed by two porcine brains compared with the signature of the interface of the skull backed by the two porcine brains containing an intervening layer of blood. Signature data are presented as, real part, imaginary part, amplitude and phase versus frequency.

Figure 5:
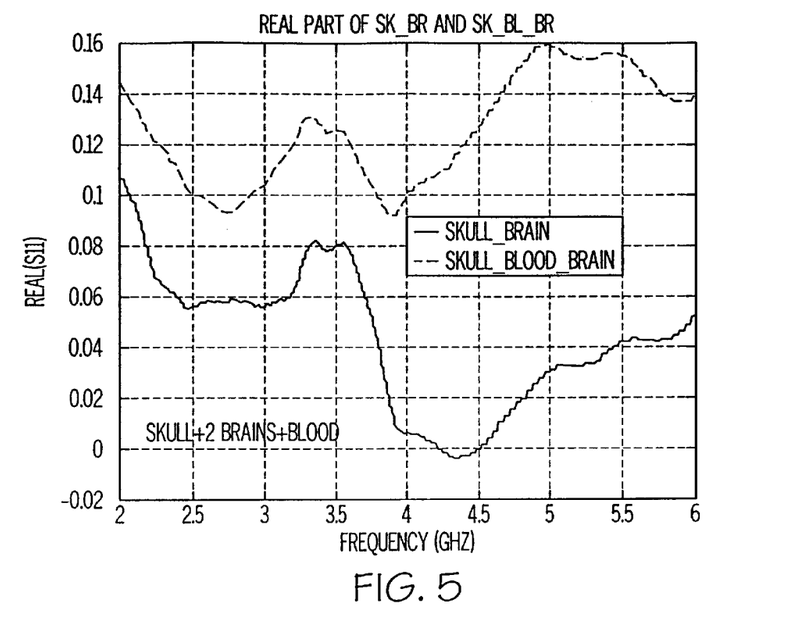
FIG. 5 illustrates the real part of Skull-Brain/Skull-Blood-Brain signatures obtained in practicing the present invention.
Figure 6:
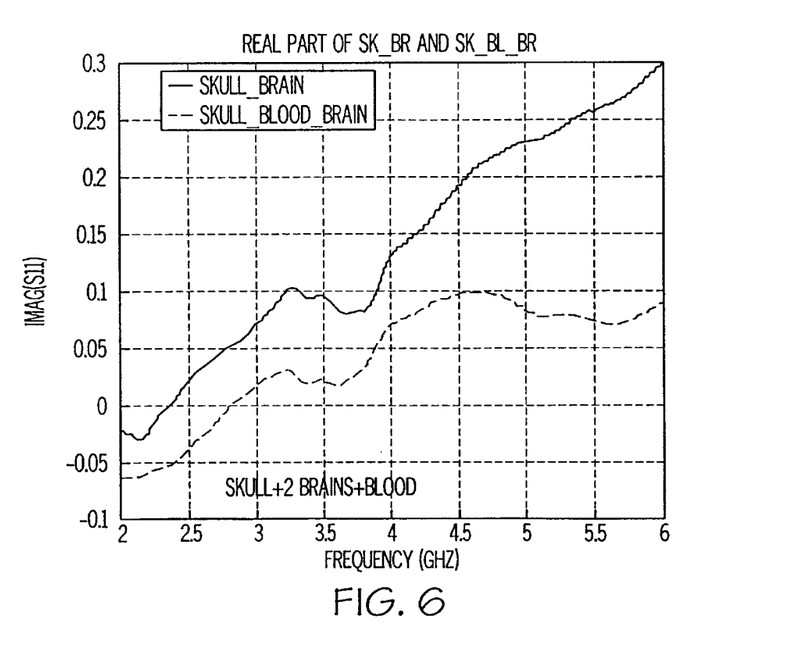
FIG. 6 illustrates the imaginary part of Skull-Brain/Skull-Blood-Brain signatures obtained in practicing the present invention.
Figure 7:
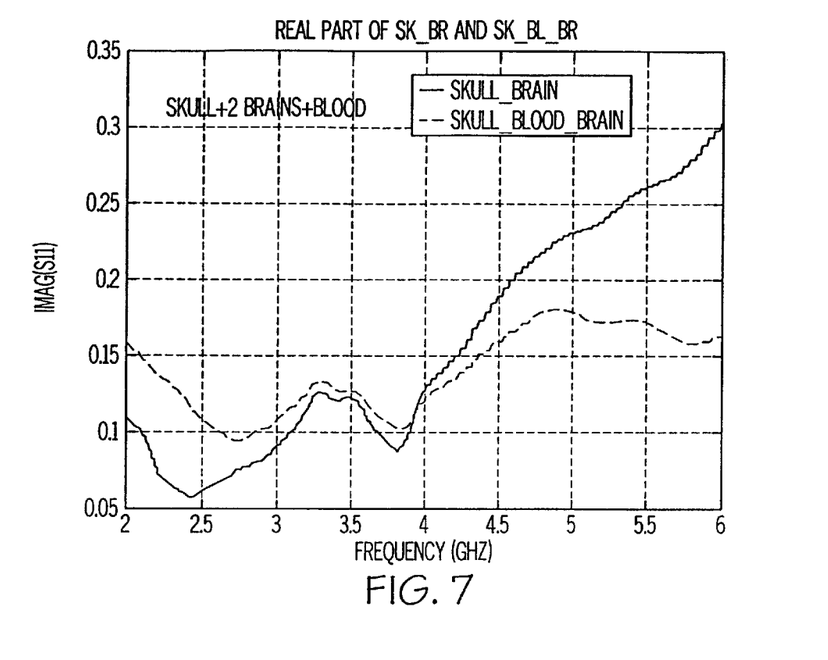
FIG. 7 illustrates the amplitude of Skull-Brain/Skull-Blood-Brain signatures obtained in practicing the present invention.
Figure 8:
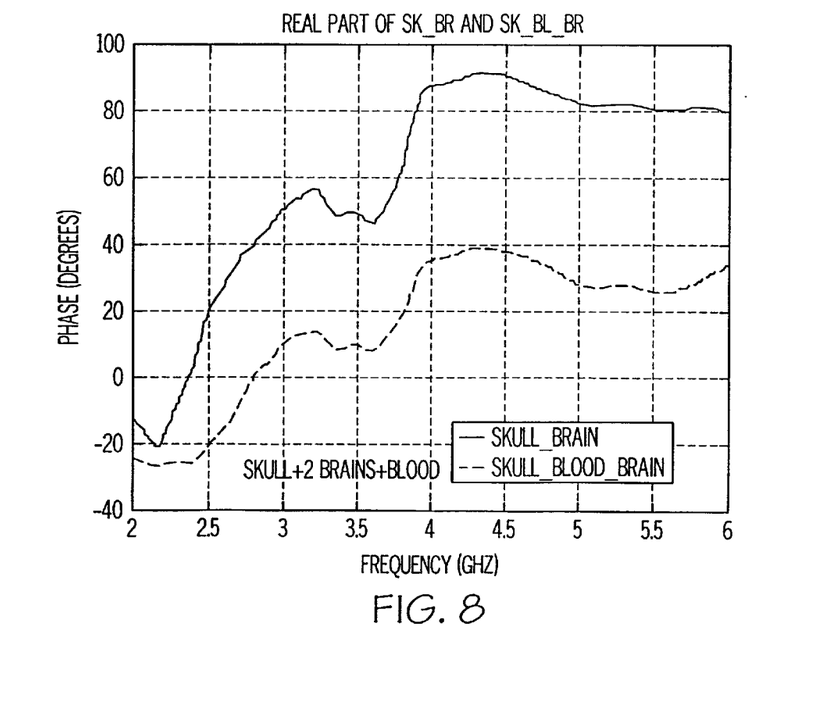
FIG. 8 illustrates the phase of Skull-Brain/Skull-Blood-Brain signatures obtained in practicing the present invention.

FIG. 5 illustrates the real part of Skull/Skull-Brain signatures for test objects with and without blood interposed between the skull and brain. FIG. 6 illustrates the imaginary part of Skull/Skull-Brain signatures for test objects with and without blood interposed between the skull and brain. FIG. 7 illustrates the amplitude of Skull/Skull-Brain signatures for test objects with and without blood interposed between the skull and brain. FIG. 8 illustrates the phase of Skull/Skull-Brain Signature for test objects with and without blood interposed between the skull and brain.

Note that there are quite discernible differences between the signatures, indicating the effect of the presence of the blood on the reflected signal. It appears that obtaining the real and imaginary parts of the backscattered signal will be the most effective way of declaring the presence of blood behind the skull. It is this effect that presents an opportunity to detect the presence or absence of subdural hematomas. Employment of standard neural net algorithms will enhance the detection probability and reduce the human interface in the system. Hemorrhage site location using microwaves offers an interesting new modality for "first responder" diagnosis and treatment of closed head injuries. The important concepts and results: 1) The detection/location technique utilizes electromagnetic backscattering, 2) This backscatter is due to discontinuities in permittivity between interfaces in the body, 3) Blood/Brain interfaces have sufficiently high contrast ratios to be detected using this technique.

It is contemplated by the present invention that the analysis techniques of the present invention will have application to a number of schemes requiring identification, location, and analysis of an embedded region within a test object. For example, in addition to hemorrhage detection, the present invention contemplates application to diagnosis of compartment syndrome and detection of pneumothorax, hemothorax, or cancerous tissue. Outside the medical imaging area, the present invention contemplates application to non-destructive evaluation of materials such as layered composites, rubber compounds, and other dielectrics. The present invention can also be utilized for determining, identifying, or quantifying material quality, corrosion, purity, anomalies, and separations in: bulk materials, plastics, microelectronic components, electronic circuit cards, crystals, visually non-transparent windows (IR windows), tires, hoses, coatings, etc. Finally, it is contemplated that the present invention may be applied to detect the presence of buried non-metallic objects such as pipes, passages, plastic mines, etc.

Having described the invention in detail and by reference to preferred embodiments thereof, it will be apparent that modifications and variations are possible without departing from the scope of the invention defined in the appended claims.

What is claimed is:

1. A method of electromagnetically detecting an embedded dielectric region within a target object comprising the steps of:

selecting a target object including a plurality of discrete scattering mediums, wherein said plurality of discrete scattering mediums include said embedded dielectric region and an adjacent dielectric region, and wherein said plurality of discrete scattering mediums define at least one dielectric interface between said embedded dielectric region and said adjacent dielectric region;

directing electromagnetic radiation at said target object, wherein said electromagnetic radiation is characterized by a diagnostic frequency that is varied incrementally over a diagnostic frequency band;

detecting electromagnetic radiation reflected by said target object over said predetermined frequency band such that there are M measurements of a reflected electromagnetic signal at frequencies $f_1, f_2, \ldots, f_N$, where M represents a number of scattering mediums within said target object and where N represents a number of diagnostic frequencies within said diagnostic frequency band;

constructing a correlation matrix representative of said reflected signal, wherein said correlation matrix comprises a number of signal eigenvectors and a number of noise eigenvectors;

decorrelating said correlation matrix by dividing said reflected signal according to frequency sub-bands within said diagnostic frequency band, wherein adjacent bands of said frequency sub-bands overlap, forming a series of iterated correlation matrices using signal eigenvectors and noise eigenvectors from each of said overlapping frequency sub-bands, forming a decorrelated matrix by averaging said iterated correlation matrices, wherein said decorrelated matrix comprises a finite group of signal eigenvectors and a finite group of noise eigenvectors; and constructing a scattering signature of said target object from said finite group of signal eigenvectors, wherein said scattering signature is indicative of the properties of said embedded dielectric region and said adjacent dielectric region.

2. A method of electromagnetically detecting an embedded dielectric region within a target object as claimed in claim 1 wherein said step of constructing said scattering signature incorporates the step of determining a frequency dependent scattering spectrum of selected ones of said discrete scattering mediums.

3. A method of electromagnetically detecting an embedded dielectric region within a target object as claimed in claim 1 wherein said scattering signature comprises a signal plot across said diagnostic frequency band.

4. A method of electromagnetically detecting an embedded dielectric region within a target object as claimed in claim 1 wherein said reflected electromagnetic signal comprises a real component and an imaginary component, and wherein said scattering signature comprises a plot of said real component across said diagnostic frequency band.

5. A method of electromagnetically detecting an embedded dielectric region within a target object as claimed in claim 1 wherein said reflected electromagnetic signal comprises a real component and an imaginary component, and wherein said scattering signature comprises a plot of said imaginary component across said diagnostic frequency band.

6. A method of electromagnetically detecting an embedded dielectric region within a target object as claimed in claim 1 wherein said scattering signature comprises a plot of the amplitude of said reflected electromagnetic signal across said diagnostic frequency band.

7. A method of electromagnetically detecting an embedded dielectric region within a target object as claimed in claim 1 wherein said method further comprises the step of substantially removing portions of said reflected signal corresponding to predetermined known scatterers, whereby signal portions of interest tend to dominate the construction of said scattering signature.

8. A method of electromagnetically detecting an embedded dielectric region within a target object as claimed in claim 7 wherein said portions of said reflected signal corresponding to predetermined known scatterers are substantially removed by constraining the noise eigenvectors to be orthogonal to the signal eigenvectors of known scatterers.

9. A method of electromagnetically detecting an embedded dielectric region within a target object as claimed in claim 1 wherein said method further comprises the step of removing portions of said reflected signal corresponding to background scatterers, whereby signal portions of interest tend to dominate the construction of said scattering signature.

10. A method of electromagnetically detecting an embedded dielectric region within a target object as claimed in claim 1 further comprising the steps of:

estimating said number of signal eigenvectors within said reflected signal; and verifying said number of signal eigenvectors within said reflected signal by plotting an eigenvalue spectrum of said correlation matrix and identifying a set of substantially equal eigenvalues.

11. A method of electromagnetically detecting an embedded dielectric region within a target object as claimed in claim 1 wherein each frequency sub-band differs from an adjacent frequency sub-band in that their respective frequency ranges are incremented relative to one another by an amount equal to the incremental variation of said diagnostic frequency.

12. A method of electromagnetically detecting an embedded dielectric region within a target object as claimed in claim 1 wherein said diagnostic frequency band extends from about 0.5 GHz to about 20.0 GHz.

13. A method of electromagnetically detecting an embedded dielectric region within a target object as claimed in claim 1 wherein said diagnostic frequency band extends from about 0.5 GHz to about 6.0 Ghz.

14. A system for electromagnetically detecting an embedded dielectric region within a target object, wherein the target object includes a plurality of discrete scattering mediums, wherein said plurality of discrete scattering mediums include said embedded dielectric region and an adjacent dielectric region, and wherein said plurality of discrete scattering mediums define at least one dielectric interface between said embedded dielectric region and said adjacent dielectric region, said system comprising:

an electromagnetic radiation source configured to direct electromagnetic radiation at said target object, wherein said electromagnetic radiation is characterized by a diagnostic frequency that is varied incrementally over a diagnostic frequency band;

an electromagnetic radiation detector configured to detect electromagnetic radiation reflected by said target object over said predetermined frequency band such that there are M measurements of a reflected electromagnetic signal at frequencies $f_1, f_2, \ldots, f_N$, where M represents a number of scattering mediums within said target object and where N represents a number of diagnostic frequencies within said diagnostic frequency band; and a data processor configured to construct a correlation matrix representative of said reflected signal, wherein said correlation matrix comprises a number of signal eigenvectors and a number of noise eigenvectors, decorrelate said correlation matrix by dividing said reflected signal according to frequency sub-bands within said diagnostic frequency band, wherein adjacent bands of said frequency sub-bands overlap, forming a series of iterated correlation matrices using signal eigenvectors and noise eigenvectors from each of said overlapping frequency sub-bands, and forming a decorrelated matrix by averaging said iterated correlation matrices, wherein said decorrelated matrix comprises a finite group of signal eigenvectors and a finite group of noise eigenvectors; and construct a scattering signature of said target object from said finite group of signal eigenvectors, wherein said scattering signature is indicative of the properties of said embedded dielectric region and said adjacent dielectric region.

15. A system for electromagnetically detecting an embedded dielectric region within a target object as claimed in claim 14 further comprising a frequency spectrum plotter in communication with said data processor, wherein said data processor is operative to cause said frequency spectrum plotter to display said scattering signature as a frequency dependent scattering spectrum of selected ones of said discrete scattering mediums.

16. A system for electromagnetically detecting an embedded dielectric region within a target object as claimed in claim 15 wherein said scattering signature comprises a signal plot across said diagnostic frequency band.

17. A system for electromagnetically detecting an embedded dielectric region within a target object as claimed in claim 15 wherein said reflected electromagnetic signal comprises a real component and an imaginary component, and wherein said scattering signature comprises a plot of said real component across said diagnostic frequency band.

18. A system for electromagnetically detecting an embedded dielectric region within a target object as claimed in claim 15 wherein said reflected electromagnetic signal comprises a real component and an imaginary component, and wherein said scattering signature comprises a plot of said imaginary component across said diagnostic frequency band.

19. A system for electromagnetically detecting an embedded dielectric region within a target object as claimed in claim 15 wherein said scattering signature comprises a plot of the amplitude of said reflected electromagnetic signal across said diagnostic frequency band.

20. A system for electromagnetically detecting an embedded dielectric region within a target object as claimed in claim 14 wherein said data processor is further configured to substantially remove portions of said reflected signal corresponding to predetermined known scatterers, whereby signal portions of interest tend to dominate the construction of said scattering signature.

21. A system for electromagnetically detecting an embedded dielectric region within a target object as claimed in claim 20 wherein said data processor is further configured to substantially remove portions of said reflected signal corresponding to predetermined known scatterers by constraining the noise eigenvectors to be orthogonal to the signal eigenvectors of known scatterers.

22. A system for electromagnetically detecting an embedded dielectric region within a target object as claimed in claim 20 wherein said data processor is further configured to substantially remove said portions of said reflected signal corresponding to background scatterers, whereby signal portions of interest tend to dominate the construction of said scattering signature.

23. A system for electromagnetically detecting an embedded dielectric region within a target object as claimed in claim 14 wherein said data processor is further configured to:

input an estimate of said number of signal eigenvectors within said reflected signal; and enable verification of said number of signal eigenvectors within said reflected signal by generating a plot of an eigenvalue spectrum of said correlation matrix.

24. A system for electromagnetically detecting an embedded dielectric region within a target object as claimed in claim 14 wherein said data processor is further configured to select each frequency sub-band such that it differs from an adjacent frequency sub-band in that their respective frequency ranges are incremented relative to one another by an amount equal to the incremental variation of said diagnostic frequency.

25. A system for electromagnetically detecting an embedded dielectric region within a target object as claimed in claim 14 wherein said electromagnetic radiation source is configured to generate said diagnostic frequency band such that it extends from about 0.5 GHz to about 20.0 GHz.

26. A system for electromagnetically detecting an embedded dielectric region within a target object as claimed in claim 14 wherein said electromagnetic radiation source is configured to generate said diagnostic frequency band such that it extends from about 0.5 GHz to about 6.0 GHz.

* * * * *